United States Patent [19]
Oliver et al.

[11] Patent Number: 5,897,987
[45] Date of Patent: Apr. 27, 1999

[54] USE OF ARABINOGALACTAN IN CELL CRYOPRESERVATION MEDIA

[75] Inventors: Sylvia Adams Oliver, Spokane; Joanna E. Ellington, Valleyford, both of Wash.

[73] Assignee: Advanced Reproduction Technologies, Inc., Spokane, Wash.

[21] Appl. No.: 08/621,489

[22] Filed: Mar. 25, 1996

[51] Int. Cl.$^6$ ................................ C12N 1/00; C12N 1/04
[52] U.S. Cl. ........................ 435/1.3; 435/243; 435/260; 435/325; 435/404; 536/123.1
[58] Field of Search ..................... 435/243, 260, 435/1.3, 325, 404, FOR 100, FOR 101, FOR 112, FOR 113; 536/123.1

[56] References Cited

U.S. PATENT DOCUMENTS

| | | | |
|---|---|---|---|
| 4,004,975 | 1/1977 | Lionetti et al. | 195/1.8 |
| 4,007,087 | 2/1977 | Ericsson | 195/1.8 |
| 4,327,177 | 4/1982 | Shrimpton | 435/2 |
| 4,605,558 | 8/1986 | Shrimpton | 424/105 |
| 5,071,741 | 12/1991 | Brockbank | 435/1 |
| 5,116,969 | 5/1992 | Adams et al. | 536/128 |
| 5,405,742 | 4/1995 | Taylor | 435/1 |
| 5,478,576 | 12/1995 | Jung et al. | 424/488 |

FOREIGN PATENT DOCUMENTS

| | | |
|---|---|---|
| WO 92/08347 | 5/1992 | WIPO . |
| WO 93/25239 | 12/1993 | WIPO . |
| WO 95/06068 | 2/1995 | WIPO . |

OTHER PUBLICATIONS

Bongso, et al., "Improved Sperm Concentration Motility, And Fertilization Rates Following Ficoll Treatment Of Sperm In A Human In Vitro Fertilization Program", *Fertility And Sterility*, 51(5):850–854 (1989).

Borel–Rinkes, et al., "Long–Term Functional Recovery Of Hepatocytes After Cryopreservation In A Three–Dimensional Culture Configuration", *Cell Transplantation*, 1:281–292 (1992).

Buchala, et al., "Polysaccharides In The Culture Medium Of Cotton Cells Cultured In Vitro", Food Hydrocolloids, 1(5/6):359–363 (1987).

Charak et al., "A Novel Approach To Immunomodulation Of Frozen Human Bone Marrow With Interleukin–2 For Clinical Application", *Bone Marrow Transplantation*, 11:147–154 (1993).

CRYO '95 Program, The Society for Cryobiology, University of Wisconsin Medical School, Continuing Medical Education, Department of Surgery, and University of Wisconsin–Extension, Jul. 6–11, 1995, Madison, Wisconsin.

Degnan, et al., "Arabinogalactan Utilization In Continuous Cultures Of Bifidobacterium Longum: Effect Of Co–Culture With Bacteroides Thetaiotaomicron", *Anaerobe*, 1:103–112 (1995).

Fahy, "Equations For Calculating Phase Diagram Information For The Ternary Systems NaCl–Dimethylsulfoxide–Water And NaCl–Glycerol–Water", *Biophys, J.*, 32:837–850 (1980).

Fahy, "Cryoprotectant Toxicity And Cryoprotectant Reduction: In Search Of Molecular Mechanisms[1]", *Cryobiology*, 27:247–268 (1990).

Feng et al., "Improved Endothelial Viability Of heart Valves Cryopreserved By A New technique", *Eur. J. Cardiothorac. Surg.*, 6:251–255 (1992).

Hagenah and Bohnke, "Corneal Crypreservation With Chondroitin Sulfate", *Cryobiology*, 30:396–406 (1993).

Hill, et al., "Use Of Arabinogalactan To Obtain Washed Murine Platelets Free Of Contaminating Plasma Proteins And Appropriate For Studies Of Function, Morphology, And Thromboiesis," *J. Lab. Clin. Med.*, 111:73–83 (1988).

Holtz, et al., "A Simple Saccharide Extender For Cryopreservation Of Rainbow Trout (Oncorhynchus Mykiss) Sperm," *Proc. Fourth Intern. Symp. Repr. Phys. Fish.* (1991).

Klebe and Mancuso, "Identification Of New Cryoprotective Agents For Cultured Mammalian Cells", In Vitro, 19:167–170 (1983).

Lovelock, "The Haemolysis Of Human Red Blood–Cells by Freezing And Thawing", *Biochem. Biophys. Acta*, 10:414–446 (1953).

Maisse, "Comparaison de l'effet cryoprotecteur de différents gludies sur le sperme de truite arc–en–ciel (Oncorhynchus mykiss)," *Aquat. Living Resour.*, 7:217–219 (1994).

Mazur, "Freezing Of Living Cells; Mechanisms And Implications", *Am. J. Physiol.*, 247:C125–142 (1984).

Mosmann, "Rapid Colorimetric Assay For Cellular Growth And Survival: Application To Proliferation And Cytotoxicity Assays", *J. Immunol. Methods.*, 65:55–63 (1983).

Parrish, et al., "Effect Of Bovine Sperm Separation By Either Swim–Up Or Percoll Method On Success Of In Vitro Fertilization And Early Embryonic Development", *Theriogenology*, 44:859–869 (1995).

Pegg, "Perfusion Of Rabbit Kidneys With Cryoprotective Agents", *Cryobiology*, 9:411–419 (1972).

Paltov, et al., "Freezing Of Ram Sperm In Media Containg Polysaccharides", *Oytseyodstyo*, 10:38–39 (1980) (Abstract).

(List continued on next page.)

*Primary Examiner*—Michael G. Wityshyn
*Assistant Examiner*—Deborah K. Ware
*Attorney, Agent, or Firm*—Seed and Berry LLP

[57] ABSTRACT

Methods and compositions for cryopreserving somatic cells are provided. In one embodiment, a cell cryopreservation medium is provided which includes an effective amount of arabinogalactan to maintain the viability of cells upon freezing, storage and thawing. The cells may be cooled or frozen during storage to a temperature about or below 4° C., for example, to about –196° C. In one preferred embodiment, ultrarefined arabinogalactan is provided in the cryopreservation medium, optionally in combination with a second cryopreservation agent, such as dimethyl sulfoxide. The medium can be used for the cryopreservation of a wide variety of different cell types from different sources. For example, mammalian cells, including porcine, canine, human, equine, rodent and bovine cells can be cryopreserved in the medium. The presence of arabinogalactan in the medium protects the viability of cells in the medium during the process of freezing, storage and thawing.

22 Claims, No Drawings

OTHER PUBLICATIONS

Prescott, et al., "Larch Arabinogalactan For Hepatic Drug Delivery: Isolation And Characterization Of A 9 kDa Arabinogalactan Fragment," *Carbohydrate Research*, 278:113–128 (1995).

Shier and Olsen, "Isotonic Sucrose Improves Cryopreservation Of Culture Mannalian," In Vitro Cell Dev. Biol., 31:336–337, 1995).

Smith, et al., "Use Of Postseparation Sperm Parameters To Determine The Method Of Choice For Sperm Preparation For Assisted Reproductive Technology", *Fertility And Sterility*, 63(3):591–597 (1995).

Stout, "Larch Arabinogalactan" in Industrial Gums, R.L. Whistle Ed., Academic Press, New York, 307–310 (1959).

Swanson, et al., "Effect Of Percoll Wash On Sperm Motion Parameters And Subsequent Fertility In Intrauterine Insemination Cycles", *J. Assisted Repro. And Genetics*, 12(1):48–54 (1995).

Tanphaichitr, et al., "Egg–Penetration Ability And Structural Properties Of Human Sperm Prepared By Percoll–Gradient Centrifugation", *Gamete Research*, 20:67–81 (1988).

USE OF ARABINOGALACTAN IN CELL CRYOPRESERVATION MEDIA

BACKGROUND OF THE INVENTION

The present invention is generally in the area of media containing arabinogalactan for use in the cryopreservation of somatic cells.

Long-term storage of somatic cells and tissues is of widespread critical importance to the research and biomedical fields. Cryopreservation of cells and tissues is useful, for example, for the storage of blood products for clinical use; the establishment of organ banks; the long-term storage of cell lines to provide an unchanging population of cells; and the storage of populations of cells for research or medical purposes.

Somatic cells can be stored indefinitely once they reach liquid nitrogen temperature (−196° C.). It has been well-established, however, that the freezing process itself results in immediate and long-term damage to cells with the greatest damage occurring to cells as they traverse the intermediate zone of temperature (−15° C. to −60° C.) during cooling and thawing (Mazur, *Am. J. Physiol.*, 247:C125–142, 1984). The primary damaging physical events which can occur to cells during the process of freezing include dehydration and intracellular ice crystal formation. During freezing, solute is rejected from the solid phase producing an abrupt change in concentration in the unfrozen portion of solution. A biological cell responds to this perturbation by dehydrating to reach a new equilibrium state between intracellular and extracellular solutions. At high cooling rates, equilibrium cannot be maintained because the rate at which the chemical potential in the extracellular solution is being lowered is much greater than the rate at which water can diffuse out of the cell. The end result of this imbalance is that intracellular ice formation (IIF) is observed which is lethal to the cell. Toner, *J. of Applied Phys.*, 67:1582–1593 (1990). At low cooling rates, cells are exposed for long periods of time at high subzero temperatures to high extracellular concentrations resulting in potentially damaging high intracellular concentrations. Lovelock, *Biochem. Biophys. Acta*, 10: 414–446 (1953).

The clinical and commercial application of cryopreservation for certain cell types is limited by the ability to recover a significant number of total viable cells. Significant losses in cell viability are observed in certain primary cell types. Examples of freeze-thaw cellular trauma have been encountered with cryopreservation of hepatocytes (Borel-Rinkes et al., *Cell Transplantation*, 1:281–292, 1992) porcine corneas (Hagenah and Bohnke, 30:396–406, 1993), bone marrow (Charak et al., *Bone Marrow Transplantation*, 11:147–154, 1993) and porcine aortic valves (Feng et al., *Eur. J. Cardiothorac. Surg.*, 6:251–255, 1992).

Cryopreservation protocols typically require the use of cryoprotective agents ("CPAs") to achieve clinically relevant survival rates for mammalian cells. A variety of substances have been used or investigated as potential additives to enhance survival of cells in the freezing process. The two most commonly used substances are glycerol and dimethyl sulfoxide. Other substances used include sugars, polymers, alcohols and proteins. CPAs can be divided roughly into two different categories; substances which permeate the cell membrane; and impermeable substances. One mechanism of protection results from reduction in the net concentration of ionic solutes for a subzero temperature when a CPA is present. This colligative effect is true for all substances which act as a CPA (Fahy, *Biophys. J.* 32:837–850, 1980). The addition of a CPA, however, changes the ionicity of the solution. Both tissues and intact organs can exhibit reduced cellular viability when exposed to sufficiently large step changes in external osmolarity produced by introduction of a freezing solution. Pegg, *Cryobiology*, 9:411–419 (1972). In addition, long term exposure to even low concentrations of certain CPAs at room temperature is potentially damaging (Fahy, *Cryobiology*, 27:247–268, 1990). Two of the most widely used cryopreservative agents, dimethylsulfoxide ("DMSO") and glycerol, are damaging to thawed cells due to osmotic complications and must be removed from cells post-thaw via rinsing and centrifugation.

Another media component routinely added to freezing media to reduce cell damage and death during freezing and thawing is serum. This additive, however, is highly complex and may add a number of factors (known and unknown) which may interfere with or alter cell function. Other non-permeating protective agents such as ethylene glycol, polyvinyl pyrrolidone (Klebe and Mancuso, *In Vitro*, 19:167–170, 1983) sucrose, and culture medium (Shier and Olsen, *In Vitro Cell Dev. Biol.*, 31:336–337, 1995), have been studied for their effectiveness as cryoprotective agents for cells with variable results.

U.S. Pat. No. 4,004,975 to Lionetti et al. discloses the cryopreservation of leukocytes from centrifuged blood in a solution of hydroxyethyl starch and dimethylsulfoxide. U.S. Pat. No. 5,071,741 to Brockbank and PCT WO 92/08347 to Cryolife, published May 29, 1992, disclose the use of algae-derived polysaccharides such as agarose and alginate in a cryoprotective cell medium. U.S. Pat. No. 5,405,742 to Taylor discloses a solution for use as a blood substitute and for preserving tissue which includes dextran.

PCT WO 95/06068 (Abstract) discloses the use of polysaccharides in to improve hematopoietic functions and serve as a radioprotective agent. The use of gum arabic, cherry resin and apricot resin in ewe semen freezing medium is disclosed in Platov et al., *Ovtsevodstvo*, 10:38–39 (1980) (Abstract). Holtz et al., *Proc. Fourth Intern. Symp. Repr. Phys. Fish*, (1991) discloses the use of saccharides such as glucose and sucrose in the cryopreservation of trout semen. Hill et al., *J. Lab. Clin. Med.*, 111:73–83 (1988) discloses the use of arabinogalactan to obtain washed murine platelets by centrifugation. Maisse, *Aquat. Living Resour.*, 7:217–219 (1994) discloses a study of the effect of carbohydrates such as glucose and maltose on the cryopreservation of trout sperm. Isotonic sucrose in combination with calf serum has been used in a medium for the cryopreservation of mammalian cells. Shier and Olsen, *In Vitro Cell. Dev. Biol.*, 31:336–337 (1995).

The preparation of derivatives of arabinogalactan and arabinogalactan degradation products is described in Prescott et al., *Carbohydrate Research*, 278:113–128 (1995); and U.S. Pat. No. 5,478,576 to Jung et al., the disclosures of which are incorporated herein by reference.

There is a need for additives which can be added to cell freezing media which stabilize cells during freezing, and protect cells from damage, which are non-toxic, and are suitable for a wide range of cell types in a wide variety of cell culture and clinical applications.

It is therefore an object of the invention to provide improved media for the preservation of somatic cells during freezing. It is a further object of the invention to provide media which can be used to preserve somatic cells and maintain the viability of the cells upon freezing and thawing. It is another object of the invention to provide media which can be used for the cryopreservation of a wide range of different somatic cell types.

SUMMARY OF THE INVENTION

Methods and compositions for cryopreserving somatic cells are provided. In one embodiment, a cell cryopreservation medium is provided which includes an effective amount of arabinogalactan to maintain the viability of cells upon freezing, storage and thawing. The cells may be cooled or frozen during storage to a temperature about or below 4° C., for example, to about −200° C. Preferably, the medium is frozen to a temperature between about −70° C. and −200° C. In one preferred embodiment, ultrarefined arabinogalactan is provided in the cryopreservation medium, optionally in combination with a second cryopreservation agent, such as dimethyl sulfoxide. The medium can be used for the cryopreservation of a wide variety of different cell types from different sources. For example, mammalian cells, including porcine, canine, human, equine, rodent and bovine cells can be cryopreserved in the medium. The presence of arabinogalactan in the medium protects the viability of cells in the medium during the process of freezing, storage and thawing.

DETAILED DESCRIPTION OF THE INVENTION

Methods and compositions are provided for the cryopreservation of somatic cells and tissues. In one embodiment, media including ultrarefined arabinogalactan and methods for use of the media in cryopreserving cells to protect cell viability upon freezing and thawing are provided. In the process, arabinogalactan serves as a nonpermeating cryoprotective agent, and advantageously exerts no effect on the osmolality of the extracellular environment.

Arabinogalactan

Arabinogalactan is a water-soluble polysaccharide which can be isolated from species of the genus Larex. Arabinogalactan may constitute up to 35% of the total heartwood of some species. Stout, "Larch Arabinogalactan" in *Industrial Gums*, R. L. Whistle Ed., Academic Press, N.Y., pp. 307–310, 1959. It is highly soluble and can be obtained at 95% purity from larch chips. Impurities present are largely monomeric sugars, polyphenols and salts. In a preferred embodiment, ultrarefined arabinogalactan, which is highly purified, is used in the cell freezing medium. Methods for the preparation of ultrarefined arabinogalactan are disclosed in U.S. Pat. No. 5,116,969, the disclosure of which is incorporated herein by reference. Ultrarefined arabinogalactan of greater than 95%, or optionally, greater than 99.9% purity (LAREX UF™) is available from Larex, International, St. Paul, Minn. Ultrarefined arabinogalactan advantageously makes little or no contribution to the osmolality of aqueous solutions in which it is a solute. Ultrarefined arabinogalactan advantageously is highly stable, non-toxic, and water-soluble.

As used herein, the term "arabinogalactan," unless otherwise specified, includes naturally occurring or synthetic arabinogalactan, portions of arabinogalactan, such as degradation products, and chemically or biochemically modified arabinogalactan or portions thereof which have been modified using methods available in the art, which are effective in a somatic cell cryopreservation medium to protect somatic cell viability properties upon freezing and thawing of somatic cells in the medium.

As defined herein "ultrarefined arabinogalactan" refers to arabinogalactan, isolated from a plant source such as trees of the genus Larix, with a purity greater than 95%. The molecular weight of the arabinogalactan in one embodiment ranges from about 6,000 to 2,500,000. In another embodiment, the molecular weight of the ultrarefined arabinogalactan is between about 10,000 and 30,000 daltons (by size exclusion chromatography with pullulan reference).

Arabinogalactan provides a useful low cost alternative to the use of DMSO or serum in cell cryopreservation media. Arabinogalactan from Larix species is useful since it is extremely water-soluble, occurs naturally with a very narrow molecular weight distribution, and is highly branched and thus not subject to viscosity problems.

Cell Cryopreservation Media

In one embodiment, the cell medium is formed by adding ultrarefined arabinogalactan powder, such as LAREX UF™, available from Larex, International, St. Paul, Minn., to a balanced salt solution, suitable for a specific cell type, wherein the concentration of ultrarefined arabinogalactan is sufficient to protect post-thaw viability of cells upon freezing, storage and thawing. In a preferred embodiment, the arabinogalactan is dissolved within the cell cryopreservation medium, however, the media also may include formulations in which arabinogalactan is dispersed.

The cell cryopreservation medium is prepared by adding an effective concentration of arabinogalactan to a simple medium such as a balanced salt tissue or cell culture medium designed for a specific cell type. The concentration of arabinogalactan can be as high as the maximum concentration of arabinogalactan that is soluble in the cryopreservation medium, and typically ranges from between 5 and 70% (wt./vol.) in the cryopreservation medium. The concentration of arabinogalactan is generally between about 20 and 50%, preferably between about 44 and 50% (weight/volume). Dulbecco's Minimal Essential Medium ("DMEM") is the preferred medium for many cell types. Other compositions may be added to the cell media, such as amino acids, cytokines, lipids, growth factors, albumins, antibiotics, antimycotics, albumins, steroid hormones, and protein hormones. Specialized cell culture media available in the art, which are designed and optimized for a particular cell type, may be used.

In addition to arabinogalactan, optionally, one or more additional cryoprotective agents may be included in the medium prior to storage. As used herein, the term "cryoprotective agent" refers to a synthetic chemical or natural compound which inhibits cell damage during the events of freezing and thawing. In one embodiment, arabinogalactan is provided in the medium in combination with DMSO. The concentration of DMSO can range, for example, from about 1 to 10% (volume percent) in the medium. Additional cryoprotective agents which can be added to the cryopreservation medium include serum, growth factors, glycerol, hyaluronic acid, dermatan sulfate, heparin sulfate, chondroitin sulphate, serum albumin, heparin, polyvinyl pyrrolidone, starches, celluloses, polyethylene glycol, propylene glycol, and N,N-dimethylformamide. Serum formulations available in the art may be added to the medium, such as fetal bovine serum, for example at a concentration between about 10 and 40% (volume percent), or bovine neonatal serum. In some embodiments, serum is included in the freezing medium containing arabinogalactan together with additional permeating cryoprotective agent such as DMSO. The medium can be readily adjusted for a particular cell sample.

The presence of arabinogalactan in the media, alone or in combination with other cryoprotective agents, reduces cellular damage due to the cryopreservation process and increases post-thaw viability. While not being limited to any theory, it is possible that the protective effect during freezing may occur by altering the formation of extracellular ice crystals and reduction of cellular osmotic dehydration during the cryopreservation process.

Cell Freezing Procedures

Cells or tissue can be obtained from commercial suppliers or using methods available in the art. The cryopreservation medium is added to a cell pellet or tissue sample, and the Medium is mixed thoroughly with the cells, or the tissue is immersed in the medium, and the medium containing the tissue or cell sample is cooled or frozen, for example, to the temperature of liquid nitrogen.

In an exemplary procedure, ultrapurified AG is prepared at a 50% weight/volume ("w/v") concentration in a buffered isotonic salt solution. This solution then is filter-sterilized (0.2 $\mu$m) and either used directly as the cryopreservative medium or, for example, in combination with DMSO (depending upon cell type). Cells to be frozen are enumerated, concentrated by centrifugation, resuspended in the freezing medium of choice (e.g., AG or AG+DMSO;1× $10^6$–$1\times10^7$ cells/vial), aliquoted into 1.8 ml cryovials (Nunc), equilibrated for about 30 minutes at 4° C., step-cooled for 18 hours at −80° C., and immediately transferred to liquid nitrogen (−196° C.). It may be preferable to chill the cell sample and the cryopreservation medium, e.g., to about 4° C., when using potentially cytotoxic cryprotective additives such as DMSO or glycerol, to reduce osmotic stress or damage to the cells. If a permeating cryoprotectant is not used in the freezing medium, the temperature at which the freezing medium is added to cells or tissues is not a critical factor. Cells are thawed by agitation of the vial in 37° C. water until only a few ice crystals remain, then are immediately diluted in an appropriate volume of culture medium specific to the cell type being cultured. If a permeating cryoprotectant such as DMSO is not used, further handling of the sample is not required prior to culture, since the freezing medium including arabinogalactan is not toxic to cells. Removal of a cell permeating or cell damaging cryoprotectant such as DMSO or glycerol can be implemented by dilution with culture medium or by cell washing, e.g., by centrifugation.

Cells frozen in either AG alone, or in AG plus DMSO exhibit at least equivalent post-thaw viability compared to a standard freezing medium containing DMSO, culture medium and serum as measured by a six-day in vitro growth test. The advantages of the use of arabinogalactan over the use of serum include minimal pathogen risk, fewer storage problems because the arabinogalactan is not toxic to cells, no protein contaminants which can interfere with protein assays or studies, lower cost, more reproducible products, and suitability for a wide variety of different cell types. The use of arabinogalactan also is advantageous due to its low viscosity and low contribution to the osmolarity of the solution. Arabinogalactan further is not toxic to cells, but rather is highly compatible with a wide variety of different cell types.

Cells Types

Any of a wide range of somatic cells can be cryopreserved in a medium including arabinogalactan as disclosed herein. A wide variety of cell types isolated from a variety of species can be cryopreserved in the medium including arabinogalactan. As used herein, the term "somatic cell" refers to any cell that is not a gamete (sperm or oocyte) or a totipotent cell such as embryonic cells; and the term "tissue" refers to a plurality of similar cells which have retained their intercellular connections and in vivo architecture, including, e.g., muscle tissue, nerve tissue, connective tissue and epithelium.

Exemplary somatic cells which can be cryopreserved include, for example, epithelial, connective tissue, muscle, amniocyte, nerve, brain, mucosal, blood, cartilage, mammary, kidney, liver, pancreatic, bone, corneal, arterial, lung, and skin cells. Somatic cells derived, for example, from the circulatory system can be cryopreserved. Mammalian cells including porcine, canine, human, murine, equine and bovine cells can be cryopreserved. In another embodiment, somatic avian cells, tumor cells, or genetically altered cells may be cryopreserved in the arabinogalactan-containing medium.

Arabinogalactan Products

Arabinogalactan ("AG") formulations can be provided, for example, in the form of a sterile 50% solution of AG syrup diluted in a buffered isotonic salt solution in, for example, 50, 100 and 500 ml bottles. This solution can then either be used directly for cell cryopreservation or mixed with DMSO and/or the cell culture medium of choice. Pre-made concentrations of arabinogalactan, in combination with DMSO and or culture medium can be provided and designed for different cell types.

Assays of Cell Viability

The viability of a cell after freezing and thawing, including the ability to maintain normal cell function, can be tested using methods available in the art. Viability of cells after freezing and thawing can be assessed, for example, by measuring rates of cell growth, measuring metabolic functions or determining the ability of cell(s) to exclude vital dyes.

A common assay used to test the viability of cultured cells is the MTT assay (Mosmann, *J. Immunol. Methods.,* 65:55–63, 1983). The basis of the MTT assay is the conversion of MTT (tetrazolium salt (3-(4,5-dimethyl-thiazol-2yl) -2,5-diphenyltetrazolium bromide) to an insoluble blue formazan crystal by mitochondrial dehydrogenases. The amount of formazan crystal formed is directly proportional to numbers of metabolically active cells. Briefly, cells are cultured for a 4-hour period in an MTT solution (100 $\mu$l of a 500 $\mu$g/ml solution per well of a 96-well plate). Following this incubation, the MTT medium is aspirated, cells are rinsed with PBS, and the resulting formazan crystals dissolved in propanol or DMSO. The 96-well plates are then read using a microplate reader set at an absorbance of 580 nm. Cell viability can be expressed either as a percent of control or can be expressed in absolute cell numbers using a standard curve derived from serial dilutions of cells cultured in serum-containing medium.

The vital dye exclusion assay is based on the ability of live, intact cells which have healthy membranes to exclude certain large molecular weight dyes such as trypan blue. In this assay, a sample of cells is mixed with the trypan blue dye. The cells can immediately be examined microscopically to determine which cells have excluded the dye. Those cells which have taken up the dye and appear blue in color are assumed to be dead and have a non-intact membrane. Cells are enumerated using a hemocytometer at a magnification of 100X. Total numbers of cells are counted and compared to the number of blue cells. The total number of cells in five squares of the hemocytometer are counted. This number is divided by five with the resulting number multiplied by 10,000 to give the number of cells per ml of original solution.

The present invention will be further understood by the following non-limiting examples.

EXAMPLE 1

Isolation of Cell Types

Cells can be isolated from a variety of tissues including, but not limited to: mammary (epithelial, stromal, endothelial, macrophage, myoepithelial), blood vessels (endothelial, smooth muscle), liver (hepatocytes, Kupfer cells), kidney (glomeruli cells), skin (fibroblasts), brain (neurons), pancreas (islet cells), blood (immune cells), lung (epithelial, alveolar macrophages), or salivary glands (fibroblasts, epithelial). Isolation procedures are specific for specific tissues, but generally involve mincing the tissue isolate, digesting the minced tissue with an enzyme such as collagenase in a balanced salt tissue culture medium (e.g., DMEM) containing a protein such as Bovine Serum Albumin (BSA). The digested tissue is filtered to remove larger undigested tissue fragments and then transferred to tissue culture treated plates (e.g., Nalgene, Corning) for establishment of primary cultures.

Cell lines can be obtained from the American Tissue Culture Collection (ATCC). These lines are cultured, passaged and stored by ATCC and include cells from a wide variety of tissues and species. These lines are received from ATCC either in a frozen state, or already in culture.

Tissue types as mentioned above can be collected and stored for short periods of time in a balanced tissue culture medium. Tissues must be stored in a cool atmosphere (4° C.) to prevent metabolic degradation. It is more difficult to maintain larger sized tissue fragments due to the inability of cells located in the central portion of the tissue to obtain necessary nutrients and oxygen. Tissue pieces also have less controlled freeze-thaw rates resulting in a wide variance in changes in chemical potential being generated during the freezing process between cells and greater damage to cells due to dehydration and intracellular ice formation.

EXAMPLE 2

Cell Cryopreservation in an Arabinogalactan=Containing Medium

The viability of different cell types after freezing in a medium with and without arabinogalactan was studied. Ultrarefined arabinogalactan ("AG") was prepared as a 50% (weight/volume) concentrated stock dissolved in a buffered isotonic salt solution. This concentrated stock was then used either directly as the cryopreservative medium or was used in combination with culture medium (depending upon cell type), DMSO and/or serum in the following ratio amounts:

TABLE 1

Cryopreservation Medium: Ratio of Components

| Medium | Culture medium | DMSO | Serum | AG |
|---|---|---|---|---|
| 1 | 7 | 1 | 2 | 0 |
| 2 | 7 | 1 | 0 | 2 |
| 3 | 0 | 0 | 0 | 10 |
| 4 | 5 | 1 | 0 | 4 |
| 5 | 5 | 1 | 2 | 2 |
| 6 | 5 | 0 | 2 | 3 |

The following seven cell types were tested:

Mouse mammary epithelial cells (NMuMG; ATCC);
Normal rat kidney epithelial cells (NRK; ATCC);
Rat liver epithelial cells (Clone 9; ATCC);
Human dermal fibroblasts (BUD 8; ATCC);
Bovine pulmonary artery endothelial cells (CPAE; ATCC);
Preneoplastic mouse mammary cells (-SA, obtained from Dr. H. Hosick, Washington State University); and
Mink lung fibroblasts (MiCl; ATCC).

Each of the above cells types was frozen in the following manner. Confluent cultures of cells were trypsinized, and concentrations of 1,000,000 cells were diluted in 1.5 ml of each of the six different freezing media. Vials were cooled at 4 C for 30 min and transferred to a −70 C freezer for 18 hours. Vials were then plunged in liquid nitrogen for storage.

The effect of the different freezing media on cell viability after freezing was determined by testing: (1) immediate post-thaw cell viability as determined using the trypan blue exclusion assay; (2) Day 1 plating efficiency (number of cells able to attach and remain viable one day after plating in standard serum-containing medium) as determined using the MTT assay; (3) cell number at Days 3 and 6; and (4) ratio of cell numbers on Day 6/Day 1 to compare overall growth rates of cells between treatments.

Each cell type was cultured until sufficient numbers were reached to allow for two (2/7) cell types or three (5/7 cell types) replicates of cryopreservation in each of the six different freezing media. For each treatment per replicate, 10 data points were generated. Therefore, either 20 or 30 data points were generated for each treatment per cell type. Data were analyzed both within cell type and between all cell types. ANOVA was used to compare all treatment groups against the industry standard freezing medium.

Immediate Post-thaw Viability

For all cell types tested, there was substantially no difference ($p>0.25$) in immediate post-thaw viability for cells frozen with arabinogalactan with or without DMSO compared to the industry standard (cell culture medium+serum+DMSO). There was a significant reduction in viability of cells frozen in arabinogalactan and serum without DMSO ($p=0.0075$).

Day 1 Plating Efficiency

This parameter measures the ability of somatic cells to attach to culture plates and remain viable post-thaw. This is an important variable to measure as cells may have apparent intact membranes (positive viability) immediately post-thaw as measured by the trypan blue exclusion assay, but may not be able to attach normally to culture plates and begin to divide.

For six of seven cell types tested, there was substantially no difference ($p>0.1$) in cell numbers on Day 1 between cells frozen in arabinogalactan and DMSO as compared to the industry standard. For all cell types, cells frozen in a combination of DMSO+serum+arabinogalactan consistently had high Day 1 plating efficiency.

Day 6 Cell Viability

This parameter gives an indication of the growth rate of cells over six days in culture in standard serum-containing serum. Analysis of data from all cells combined (within treatment) indicated substantially no difference between treatment groups ($p=0.99$).

Ratio of Day 6/Day 1 Viability

The ratio of viable cells on day 6/day 1, provides a good measure of growth rates of cells over a six-day growth period. Growth rates of cells frozen in arabinogalactan+DMSO were superior to cells frozen in standard medium ($p=0.1$). Cells frozen in arabinogalactan+serum without DMSO resulted in the poorest growth over a six-day period.

An illustrative example is provided in Table 2, which shows the ratio of cell numbers at day 6/day 1 for CPAE cells.

TABLE 2

| Medium | Growth Rates: Ranking (Day 6/Day 1) | Order |
|---|---|---|
| 1 | 79.7800 | 4 |
| 2 | 102.0588 | 3 |
| 3 | 192.2727 | 1 |
| 4 | 75.5763 | 5 |
| 5 | 146.2059 | 2 |
| 6 | 5.6149 | 6 |

Results with Different Cell Types

Arabinogalactan can be used to replace serum in a standard freezing medium, in a formulation with DMSO, for all cell types studied. AG alone (Medium 3), was used to freeze some cell types. Specifically, cell performance after freezing was either better or equivalent in Medium 3 to a standard freezing media (Medium 1) for 5 of 7 cell types tested (-SA, NMuMG, MICl, BUD-8 and CPAE).

Modifications and variations of the present invention will be obvious to those skilled in the art from the foregoing detailed description. Such modifications and variations are intended to come within the scope of the following claims.

What is claimed is:

1. A method for cryopreserving and cryoprotecting somatic cells, comprising placing the cells in a medium comprising arabinogalactan as a cryopreservative agent, wherein the medium comprises an effective concentration of the cryopreservative agent to maintain the viability, and to reduce cell damage and cell death, of somatic cells disposed therein upon freezing and thawing.

2. The method of claim 1, wherein the medium is frozen to a temperature suitable for cell freezing.

3. The method of claim 2 wherein the temperature is about or below 4° C.

4. The method of claim 2 wherein the medium is frozen to a temperature between about −70° C. and −200° C.

5. The method of claim 1 wherein the concentration of arabinogalactan in the medium is the maximum concentration soluble in the medium.

6. The method of claim 1 wherein the concentration of arabinogalactan is between about 20 and 50% (weight/volume).

7. The method of claim 1 wherein the medium comprises arabinogalactan in an aqueous buffered isotonic salt solution.

8. The method of claim 1 wherein the somatic cells are selected from the group consisting of epithelial, connective tissue, muscle, amniocyte nerve, brain, mucosal, blood, cartilage, mammary, kidney, liver, pancreatic, bone, corneal, arterial, lung, and skin cells.

9. The method of claim 1 wherein the somatic cells are derived from the circulatory system.

10. The method of claim 1 wherein the somatic cells are mammalian.

11. The method of claim 10 wherein the mammalian somatic cells are selected from the group consisting of porcine, canine, human, equine and bovine cells.

12. The method of claim 1 wherein the somatic cells are tumor cells.

13. The method of claim 1 wherein the somatic cells are genetically altered mammalian cells.

14. A cryoprotective medium comprising between 5 and 70% (weight/volume) arabinogalactan in combination with an effective amount of a second cryoprotective agent.

15. The method of claim 14 wherein the arabinogalactan is ultrarefined arabinogalactan.

16. The cryoprotective medium of claim 14 wherein the concentration of arabinogalactan in the medium is between 10 and 70% (weight/volume).

17. The cryoprotective medium of claim 14 wherein the concentration of arabinogalactan is between about 20 and 50% (weight/volume).

18. The cryoprotective medium of claim 14 wherein the medium further comprises a composition selected from the group consisting of amino acids cytokines, lipids, growth factors, antibiotics, antimycotics, steroid hormones, protein hormones and albumins.

19. The cryoprotective medium of claim 14 wherein the second cryoprotective agent is dimethyl sulfoxide ("DMSO").

20. The cryoprotective medium of claim 19 wherein the medium comprises DMSO at a concentration of between about 1 and 10% (volume percent).

21. The cryoprotective medium of claim 19 wherein the medium further comprises serum.

22. The cryoprotective medium of claim 21 wherein the medium comprises fetal bovine serum at a concentration of between about 10 and 40% (volume percent).

* * * * *